United States Patent

Whittemore et al.

[11] Patent Number: 5,824,327
[45] Date of Patent: Oct. 20, 1998

[54] KOJIC DIPALMITATE SKIN WHITENING COMESTIC COMPOSITION

[76] Inventors: Jerry Whittemore, 3300 Shelby Dr., Los Angeles, Calif. 90034; Robert Neis, 201 E. 79th St. #3J, New York, N.Y. 10021

[21] Appl. No.: 55,489

[22] Filed: Apr. 6, 1998

[51] Int. Cl.⁶ ............................. A61K 6/00; A61K 7/00
[52] U.S. Cl. ................................. 424/401; 424/45
[58] Field of Search ................ 424/62, 45, 401; 514/828, 844, 873, 969

[56] References Cited

U.S. PATENT DOCUMENTS

| | | | |
|---|---|---|---|
| 4,278,656 | 7/1981 | Nagai et al. | 424/62 |
| 4,369,174 | 1/1983 | Nagai et al. | 424/62 |
| 4,696,813 | 9/1987 | Higa | 424/59 |
| 4,847,074 | 7/1989 | Hatae et al. | 424/62 |
| 4,919,921 | 4/1990 | Hatae et al. | 424/62 |
| 4,948,577 | 8/1990 | Hara | 424/59 |
| 4,985,255 | 1/1991 | Higa | 424/583 |
| 4,985,455 | 1/1991 | Motono | 514/460 |
| 4,990,330 | 2/1991 | Oyama | 424/59 |
| 5,164,182 | 11/1992 | Meybeck et al. | 424/195.1 |
| 5,208,012 | 5/1993 | Sudo et al. | 424/59 |
| 5,279,834 | 1/1994 | Meybeck | 424/450 |
| 5,427,775 | 6/1995 | Sakai et al. | |
| 5,599,528 | 2/1997 | Igaki | 424/59 |

*Primary Examiner*—Thurman K. Page
*Assistant Examiner*—Sharon Howard
*Attorney, Agent, or Firm*—Joseph L. Spiegel

[57] ABSTRACT

A skin whitening cosmetic composition of kojic dipalmitate. When used in an anhydrous cream, the kojic dipalmitate is present in parts by weight from 0.01 to 25%, more particularly 0.2 to 8.0% and most preferably 0.4 to 4.0%. When forming an anhydrous serum, one uses the same kojic dipalmitate concentration but of a much lower viscosity. To form an anhydrous ointment, the same concentrations are used with 2–8% wax from each of the following wax groups: microcrystalline wax; animal waxes such as beeswax; vegetable waxes such as rice wax; and, hydrocarbon waxes such as paraffin. The same kojic dipalmitate concentration may be used with anhydrous alcohol to form a fine anhydrous spray.

6 Claims, No Drawings

KOJIC DIPALMITATE SKIN WHITENING COMESTIC COMPOSITION

BACKGROUND OF INVENTION

1. Field of Invention

The present invention relates to a skin whitening cosmetic composition and in particular to such a composition which is anhydrous and incorporates kojic dipalmitate.

2. Description of the Prior Art

Since the Neolithic dawn, humans have attempted to cover blemishes with cosmetics. The records of the fourth century physician Galen speaks of them in the previous millennium.

Until about 1973 dangerous agents such as ammoniated mercury had been used. Since then, Mercury derivatives have been banned from most countries.

There are some agents used to bleach skin that are so mild as to be subliminal. They include, among others, lemon, licorice, and vitamin C.

Three currently used agents have valid research to show authentic skin lightening/brightening: 2% hydroquinone, 1% kojic acid and 0.5% kojic dipalmitate.

All three are similar agents based on the pyrone nucleus. Because of the similarity of their pyrone nature, scientific studies that purport to show one to be more or less safer than the other is suspect. However, hydroquinone is now banned in many countries.

The pyrone based chemicals inhibit an enzyme in the following equation:

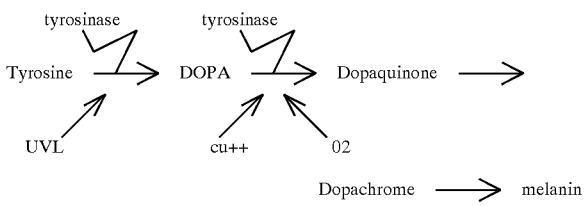

While this equation is used to rationalize several cosmetic categories (sunscreens, tanning accelerators, self tanning agents) this invention focuses on the legendary ability of pyrone based agents to interfere with the enzyme tyrosinase which retards the motion of this equation, slows down the formation of melanin and reduces melanin caused pigmentation.

While the text of these agents is the reduction of age spots or liver spots, the subtext of their key commercial value is the lightening or brightening the skin.

As a practical matter, virtually all commercial formulae utilize a chelating agent such as EDTA 0.2% to chelate the cu++ ions and help slow the mass action (to the right) of the equation above.

Surprisingly, the legal status of these very similar compounds is quite different; hydroquinone is listed as a category one skin lightener (at 2%) and the two kojic species are mere "cosmetics" and must avoid the drug wording, skin lightener. Kojic species are "skin brighteners" or "skin toners". They are "cosmetics only".

Nagai, et al, U.S. Pat. No. 4,278,656 form a skin whitener cosmetic composition from a kojic acid ester with an aliphatic carboxylic acid. The composition utilizes water and the non-dipalmate esters used will turn color.

The U.S. Pat. No. 4,369,174 to Nagai, et al, discloses a skin whitener cosmetic composition utilizing a kojic acid ester as an active ingredient. The composition utilizes water and will turn color.

In the U.S. Pat. No. 4,696,813 to Higa, the skin whitener cosmetic composition comprises placenta and kojic acid. It does not use esters, does utilize water and will turn color.

Hatae, et al, U.S. Pat. No. 4,847,074 relates to a kojic acid containing whitener cosmetic composition that includes cyclodextrins for improved stability, i.e. to compensate for color changes.

In Hatae, U.S. Pat. No. 4,919,921, the cosmetic composition comprises kojic acid or an ester of kojic acid and Vitamin C. The composition will change color in formulation.

Hara, U.S. Pat. No. 4,948,577 relates to a skin whitener composition comprised of kojic acid or derivatives thereof with 4-(1,1 - dimethylethyl)- $4^1$ methoxydiben-zoylmethan formulated therein. The composition will turn color, and prevents normal tanning but is not a true skin bleach.

The skin whitener cosmetic composition of Higa, U.S. Pat. No. 4,985,255 comprises placental extract of pregnant cows and kojic acid or a derivative thereof. The mixture uses water and will turn color.

Motono, U.S. Pat. No. 4,985,455 incorporates an ultraviolet absorber, B cyclodestrin and ethylendiaminetetracetic acid to eliminate or reduce discoloration in a kojic acid or derivatives thereof skin whitener cosmetic composition.

In Oyama, U.S. Pat. No. 4,990,330, an amino compound is included in a kojic acid or an ester thereof skin whitener cosmetic composition to inhibit melanin synthesis.

The lightening composition of Meybeck, et al, U.S. Pat. No. 5,164,182 is a composition containing a mulberry extract incorporated into hydrated lipidic lamellar phases of liposomes.

The anti-sunburn cosmetic compound of Sudo, et al, U.S. Pat. No. 5,208,012 utilizes a hydroxyaryl-s-triazine compound as the active ingredient. It offers no real skin lightening.

In the whitener composition of Maybeck, U.S. Pat. No. 5,279,834 hydroquinone and/or kojic acid or a derivative thereof is partially incorporated into liposomes.

In Sakai, et al, U.S. Pat. No. 5,427,775 the whitening composition comprises teprenone and one or more substances selected from the groups consisting of kojic acid, L-ascorbic acid and arbutin.

Igaki, U.S. Pat. No. 5,599,528 is concerned with the problem of the decomposition and discoloration of the kojic acid and utilizes a surfactant to depress same. In contrast, my invention is anhydrous with no possibility of aqueous or hydrolisis.

SUMMARY OF THE INVENTION

An object of the present invention is a skin whitening cosmetic composition which maintains its skin whitening activity while maintaining its whiteness indefinitely.

Another object is such a composition that will make a color stable, white anhydrous cream without antioxidants, preservatives or inhibitors.

The foregoing and other objects, features and advantages of the present invention are accomplished in accordance with the teachings of the present invention, one illustrative embodiment of which comprises the use of kojic dipalmitate in such a composition. When used in an anhydrous cream, the kojic dipalmitate is present in parts by weight from 0.01 to 25%, more particularly 0.2 to 8.0% and most preferably 0.4 to 4.0%. When forming an anhydrous serum, one uses the same kojic dipalmitate concentration but in a base of much lower viscosity. To form an anhydrous ointment, the same concentrations are used with 2–8% wax from each of the following wax groups: microcrystalline wax; animal waxes such as beeswax; vegetable waxes such as rice wax; and, hydrocarbon waxes such as paraffin. The same kojic dipalmitate concentration may be used with anhydrous alcohol to form a fine anhydrous spray.

DESCRIPTION OF THE PREFERRED EMBODIMENTS

Percentages of kojic dipalmitate above and below the more preferred and most preferred levels of kojic dipalmitate set forth will function within the scope and spirit of this invention and are expressed in parts by weight.

However, the skin lightening effect of the cosmetic preparation is mitigated—it takes longer—when the percentages of kojic dipalmitate is below ¼% by weight.

Moreover, when the percentages of kojic dipalmitate are raised above the 4% level, significant diseconomies develop, thus reducing the commercial value of this invention.

The essence, and the surprise, of this invention is the discovery that kojic dipalmitate will remain completely white in an anhydrous cosmetic base, maintaining its skin brightening activity but keeping its whiteness indefinitely, which increases its commercial value over hydrous formulations.

The discovery is that kojic dipalmitate will make a color stable, guaranteed white, anhydrous cream with no antioxidants, no preservatives and no inhibitors.

The chelating agent being used in the various examples is used only to sequester cu++ ions (to help mitigate the equation's going to the right) and not to prevent color change in its anhydrous final cosmetic cream.

Samples nearly a year old are as sparkling white as the day they were compounded.

The invention is exemplified, but not limited to, the formulations below:

Kojic dipalmitate anhydrous creams

| INGREDIENT | MORE PREFERRED % RANGE | | | MOST PREFERRED % RANGE | | |
|---|---|---|---|---|---|---|
| Kojic dipalmitate | 0.2 | to | 8.0 | 0.4 | to | 4.0 |
| Finetex TN (emollient) | 6.0 | | 30.0 | 10.0 | | 20.0 |
| Bernel FAO (emollient) | 3.0 | | 15.0 | 5.0 | | 10.0 |
| Cabosil M-5 (fumed silicas) | 2.0 | | 14.0 | 5.0 | | 10.0 |
| Microtitanium dioxide 95+% (sunscreen) | 0.3 | | 6.0 | 0.5 | | 3.0 |
| S D Alcohol 39C-200 | 5.0 | | 30.0 | 10.0 | | 20.0 |
| Octyl methoxycinnamate (sunscreen) | 1.0 | | 7.5 | 3.0 | | 7.5 |
| Lecithin Z-3 (emollient) | 0.5 | | 8.0 | 1.0 | | 5.0 |
| Bentone TN (hectorite compound) | 5.0 | | 28.0 | 10.0 | | 15.0 |
| Mineral Oil | 2.0 | | 16.0 | 5.0 | | 10.0 |
| Isopropyl myristate (emollient) | 8.0 | | 30.0 | 12.0 | | 20.0 |
| Fragrance | 0.08 | | 3.0 | 0.2 | | 1.0 |

Procedure: Heat the Kojic dipalmitate, Finetex, FAO, Bentone and isopropyl myristate to 70 degrees C with a jacketed kettle and add a homo mill. Slowly add, with high shear agitation, the Cabosil and the microtitanium dioxide. Mill and cool to 45–50 degrees C. Add, with milling, the remaining ingredients except the fragrance and SD alcohol. Cool with milling (and cooling jacket if needed) to 25–30 degrees C. Add, with mixing, the fragrance and alcohol. Package immediately.

Kojic Dipalmitate Anhydrous Serum

| INGREDIENT | MORE PREFERRED % RANGE | | | MOST PREFERRED % RANGE | | |
|---|---|---|---|---|---|---|
| Kojic dipalmitate | 0.2 | to | 8.0 | 0.4 | to | 4.0 |
| Octyl Salicylate (sunscreen) | 0.5 | | 3.0 | 1.0 | | 3.0 |
| Bentone TN (hectorite compound) | 1.0 | | 10.0 | 3.0 | | 6.0 |
| Lecithin Z-3 (emollient) | 0.2 | | 6.0 | 0.5 | | 2.0 |
| Lanatex IHI (emollient) | 60.0 | | 97.0 | 70.0 | | 80.0 |
| Mineral oil | 2.0 | | 16.0 | 5.0 | | 7.0 |
| Z-Cote Micro ZnO (sunscreen) | 0.2 | | 8.0 | 0.4 | | 4.0 |
| Fragrance | 0.08 | | 3.0 | 0.2 | | 1.0 |

Procedure: Heat the Lanatex IHI to 70 degrees C. Slowly dissolve the kojic dipalmitate into the kettle. Cool with mixing to about 55–60 degrees C. Add a homo mill. Slowly add, with high shear, the Cabosil M-5, the Bentone TN and the micro zinc oxide sunscreen. Cool to 35 degrees C and add, with moderate shear the remaining ingredients. Cool with mixing to 25 degrees C and package.

Kojic dipalmitate anhydrous ointments

| INGREDIENT | MORE PREFERRED % RANGE | | | MOST PREFERRED % RANGE | | |
|---|---|---|---|---|---|---|
| Kojic dipalmitate | 0.2 | to | 8.0 | 0.4 | to | 4.0 |
| Bentone TN (hectorite compound) | 6.0 | | 30.0 | 10.0 | | 20.0 |
| Cabosil M-5 (fumed silicas) | 2.0 | | 14.0 | 5.0 | | 10.0 |
| Petrolatum (emollient) | 30.0 | | 75.0 | 42.0 | | 60.0 |
| Mineral oil | 15.0 | | 60.0 | 30.0 | | 50.0 |
| Bleached Beeswax USP (wax) | 2.0 | | 15.0 | 5.0 | | 10.0 |
| Microcrystalline Wax (wax) | 2.0 | | 15.0 | 5.0 | | 10.0 |
| Octylmethoxy cinnamate (sunscreen) | 2.0 | | 10.0 | 5.0 | | 7.5 |
| Benzophenone - 3 (sunscreen) | 1.0 | | 4.5 | 2.0 | | 4.5 |
| Fragrance | 0.08 | | 3.0 | 2.2 | | 1.0 |

Procedure: Heat the carnation oil, petrolatum and the OMC in a jacketed kettle to about 65–75 degrees C. Add the two waxes and melt. When clear, add a homo mill. Slowly add, with high shear, the kojic dipalmitate, the Cabosil and the Bentone TN. Then add, with low shear, the benzophenone-3. Cool with slow mixing to 25–30 degrees C and add, with moderate shear, the fragrance. Cool to 25 degrees C and package.

Kojic dipalmitate anhydrous sprays

| INGREDIENT | MORE PREFERRED % RANGE | | | MOST PREFERRED % RANGE | | |
|---|---|---|---|---|---|---|
| Kojic dipalmitate | 0.2 | to | 8.0 | 0.4 | to | 4.0 |
| Lanatax IHI (emollient) | 20.0 | | 80.0 | 30.0 | | 65.0 |
| Bernel FAO (emollient) | 5.0 | | 20.0 | 6.0 | | 15.0 |
| Bentone TN (hectorite compound) | 2.0 | | 10.0 | 3.0 | | 6.0 |
| Octylmethoxy cinnamate (sunscreen) | 1.0 | | 10.0 | 3.0 | | 7.5 |
| Octyl salicylate (sunscreen) | 1.0 | | 8.0 | 1.5 | | 3.0 |

-continued

Kojic dipalmitate anhydrous sprays

| INGREDIENT | MORE PREFERRED % RANGE | | MOST PREFERRED % RANGE | |
|---|---|---|---|---|
| SD Alcohol 40-2 200 | 10.0 | 40.0 | 15.0 | 25.0 |
| Fragrance | 0.08 | 3.0 | 0.2 | 1.0 |

Procedure: In a suitable SS kettle, heat the Lanatex IHI to 65–75 degrees C. Add a propeller mixer. Slowly add, with slow mixing, the kojic dipalmitate. Then add with slow mixing the Bentone TN, then mix and cool to 45 to 50 degrees C and add remaining ingredients except alcohol and fragrance. Then Cool with mixing to 25 degrees C and add, with slow mixing, the fragrance and alcohol. Package.

While this invention has been described in terms of preferred embodiments, various changes and modifications can be made by those skilled in the art without departing from the spirit and scope of the invention.

What is claimed:

1. An anhydrous topical skin cream for skin whitening comprising, by weight: 0.1 to 25% kojic dipalmitate; 1–20% fumed silica base; 4–30% hectorite compound; and anhydrous ingredients selected from emollients and anhydrous alcohol.

2. The invention defined by claim 1 wherein the kojic dipalmitate is present in from 0.2 to 8.0%, by weight.

3. The invention defined by claim 1 wherein the kojic dipalmitate is present in from 0.4 to 4.0%, by weight.

4. An anhydrous skin serum comprising, by weight: 0.1 to 25% kojic dipalmitate; 1–10% fumed silica base; 0.5 to 12% hectorite compound; and emollient and sunscreen oil fluid at room temperature.

5. An anhydrous skin ointment comprising, by weight: 0.1 to 25% kojic dipalmitate; 1–20% fumed silica base; 3–35% hectorite compound; and emollients selected from waxes and oils semi-solid at room temperature.

6. An anhydrous skin spray or aerosol comprising, by weight: 0.1% to 25% kojic dipalmitate; 2 to 25% hectorite compound; and, anhydrous ingredients selected from anhydrous alcohol and ultra thin emollient oils.

* * * * *